United States Patent
Wildemeersch (12)

(10) Patent No.: US 6,742,520 B1
(45) Date of Patent: Jun. 1, 2004

(54) INTRAUTERINE CONTRACEPTIVE DEVICE

(76) Inventor: Dirk Wildemeersch, Vossenhul 8, B-8301 Knokke-Heist (BE)

( * ) Notice: Subject to any disclaimer, the term of this patent is extended or adjusted under 35 U.S.C. 154(b) by 0 days.

(21) Appl. No.: 09/979,614

(22) PCT Filed: Apr. 13, 2000

(86) PCT No.: PCT/BE00/00036

§ 371 (c)(1),
(2), (4) Date: Nov. 6, 2001

(87) PCT Pub. No.: WO00/67684

PCT Pub. Date: Nov. 16, 2000

(30) Foreign Application Priority Data

May 7, 1999 (BE) .............................................. 9900331

(51) Int. Cl.⁷ .................................................. A61F 6/06
(52) U.S. Cl. ......................... 128/830; 128/832; 128/833
(58) Field of Search ................................... 128/830–841

(56) References Cited

U.S. PATENT DOCUMENTS 4,180,064 A  * 12/1979 Heller et al. ................. 128/833
4,326,511 A  * 4/1982 Zimerman ................... 128/833
4,353,363 A  * 10/1982 Sopena Quesada ......... 128/833
4,708,134 A    11/1987 Wildemeersch
5,417,223 A  * 5/1995 Aarnio et al. ................ 128/833

FOREIGN PATENT DOCUMENTS

| DE | 4125575 | 4/1995 |
| EP | 0117163 | 8/1984 |
| FR | 2555893 | 6/1985 |

* cited by examiner

*Primary Examiner*—Michael A. Brown
(74) *Attorney, Agent, or Firm*—Collard & Roe, P.C.

(57) ABSTRACT

The present invention concerns an intrauterine device comprising a support 41, and constituents 42, 43 releasing an active ingredient.

In accordance with the invention, the active ingredient is constituted by copper with a surface area of 100 to 250 mm² and by a steroid from the progesterone family with a release rate in the range 10% to 70% of the minimum release rate employed for the steroid concerned when it is used as a contraceptive active ingredient.

With the device of the invention, contraceptive efficacy is very high and side effects are substantially reduced.

8 Claims, 1 Drawing Sheet

INTRAUTERINE CONTRACEPTIVE DEVICE

CROSS REFERENCE TO RELATED APPLICATIONS

Applicant claims priority under 35 U.S.C. §119 of BELGIUM Application No. 9900331 filed on May 7, 1999. Applicant also claims, priority under 35 U.S.C. §120 of PCT/BE00/00036 filed on Apr. 13, 2000. The international application under PCT article 21(2) was not published in English.

FIELD OF THE INVENTION

The present invention relates to an intrauterine device comprising a support and an ingredient releasing element for releasing an active ingredient, the active ingredient comprising copper and a steroid selected from the group consisting of natural progesterone, levonorgestrel and desogestrel. The copper has a surface area in the range 100 to 250 $mm^2$, and the steroid is releasable at a release rate within the following range, as a function of the steroid used:

| | |
|---|---|
| for natural progesterone | 5 to 35 µg/day; |
| for levonorgestrel | 2 to 14 µg/day; |
| for desogestrel | 0.1 to 0.7 µg/day. |

The invention has high contraceptive efficacy and significantly reduced side effects.

PRIOR ART

Intrauterine contraceptive devices are generally constituted by a support and an active ingredient released from the support.

The support is either a substantially rigid support, for example T or V-shaped, held in the uterus by dint of its shape, or a readily deformable thread or loop held in the uterus by anchoring into the wall at the fundus of the uterus.

Copper is traditionally employed as the active ingredient in intrauterine devices. Depending on the supports employed, the copper is either in the form of a coiled wire or a collar mounted on a rigid support, or in the form of elements that may or may not be hollow that are assembled together, generally by a filament, to constituent a non-rigid assembly in the form of a thread. An intrauterine device of that latter type is, for example, disclosed in the present Applicant's Belgian patent BE-A-901 652. In that publication, the intrauterine device is constituted by hollow copper elements, pierced through and disposed end-to-end to form a longitudinal channel allowing the passage of a needle, those elements being connected into a non-rigid assembly, the assembly being integral with a filament provided with a means for anchoring it in the tissue of the uterus, which can be inserted using a needle.

When copper is used as an active ingredient, until now it has been considered that the larger the surface area of copper exposed in the uterus, i.e., the larger the number of copper ions liberated into the uterus per unit time, the better the contraceptive action of the intrauterine device. This is despite the fact that copper ions are known to have a perturbing effect on homeostasis of the endometrium, in particular its coagulation capacity, and are thus capable of causing heavy bleeding during periods. This perturbing effect is, however, accepted in order to guarantee the contraceptive activity of the device. As a result, the surface area of the copper exposed in the uterus is not generally less than 250 $mm^2$. Trials carried out with conventional T or V-shaped intrauterine devices having a reduced copper surface area of 200 $mm^2$ show a failure rate (undesirable pregnancies) of 3%, which is unacceptable.

The use of steroids from the progesterone family (progesterone and progestins) as the active ingredient in the uterus is also known. Such substances have until now been contained either in a silicone support in the form of a rod, or in a porous polymer support in the form of a fibre, with characteristics that are ascertained so as to provide a release rate for the active ingredient that is suitable for the desired contraceptive activity. An intrauterine device of that type has been described in European patent EP-B-0 445 150, which is also in the name of the present Applicant.

Steroids from the progesterone family used in the uterus as an active contraceptive ingredient comprise natural progesterone and progestins, examples of which are levonorgestrel, norgestimate, gestodene, desogestrel, medroxyprogesterone acetate, etc . . .

The skilled person is well aware that such steroids do not all have the same degree of activity, and so some necessitate the use of high release rates than others. Thus, for example, when the porous polymer support contains natural progesterone, release rates until now have been in the range 50 to 100 µg/day; for levonorgestrel, the release rate range is 20 to 30 µg/day, while for desogestrel, a release rate range of 1 to 5 µg/day will not be exceeded.

Such quantities of steroids, considered until now to be necessary to guarantee a satisfactory contraceptive action, are capable of having undesirable side effects, such as systemic effects: mood changes, headaches, nausea, acne, functional ovarian cysts, or local effects: prolonged weak bleeding or amenorrhea.

Finally, intrauterine devices with a stronger contraceptive effect have been produced by combining natural progesterone and copper. Such a device has been described in German patent DE-A-4 125 575.

In that document, it is known to use a device with a copper surface area of 250 $mm^2$ and a progesterone release rate of 65 µg/day. This substantially corresponds to the copper surface areas and progesterone release rates used until now in intrauterine devices employing just one of those constituents.

Finally, EP-A-0 117 163 discloses the use of copper and progesterone together, combined with aminoisocaproic acid. That document teaches that in 1983, a copper-progesterone-aminoisocaproic acid combination was known to involve a synergistic effect between the constituents.

DE-A-4 125 575 teaches that in 1993, there was no incompatibility or contrary effects in a limited combination of copper and progesterone, since the combination was effective when the components were used in their normal quantities.

AIM OF THE INVENTION

We have now surprisingly, discovered that at the contraceptive level, there exists a synergistic effect between copper and a progestin, this effect being of a level such that, while ensuring extremely high contraceptive efficacy, the doses of the constituents, copper and a progestin, can be reduced to values such that their side effects are considerably reduced, if not completely eliminated.

This complete or almost complete absence of side effects is particularly significant in the field of contraception. While the effectiveness of the intrauterine device is guaranteed, and this is at a high level in the device of the invention, for the comfort of the user and thus for the intrauterine device to be readily accepted, its use involves a minimum of disadvantages and as few perturbations as possible.

The present invention concerns an intrauterine device for putting this discovery into practice.

In its preferred embodiments, the invention also aims to provide an intrauterine device that not only has the advantages mentioned above, but which also protects the uterus against sexually transmitted ascending infections.

DESCRIPTION OF THE DRAWINGS

The invention will be better understood from the following description made with reference to the accompanying drawings which, solely by way of example, illustrate various embodiments of the invention, and in which.

DETAILED DESCRIPTION OF THE INVENTION

Figure 1:
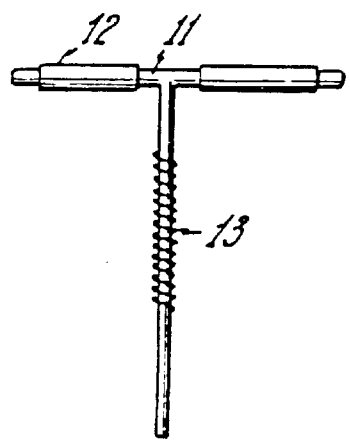
FIG. 1 shows an embodiment of an intrauterine device of the invention using a rigid T-shaped support.

The different embodiments in the drawings show an intrauterine device of the invention comprising a support and an element that releases the desired proportions of an active ingredient constituted by copper and a steroid from the progesterone family.

In FIG. 1, the support is a T-shaped support 11, with copper collars 12 mounted on the horizontal arms, and with a steroid-permeable polymer fibre 13 wound around the vertical arm, which releases a steroid from the progesterone family.

Figure 2:
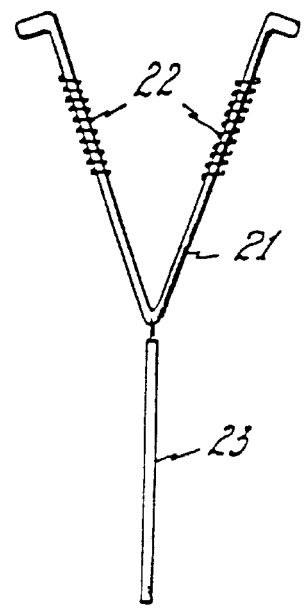
FIG. 2 shows a further embodiment of an intrauterine device of the invention using a rigid V-shaped support.

In FIG. 2, the support is a V-shaped support 21, with a copper wire 22 wound around its arms and with the lower portion attached to a porous polymer fibre 23 releasing steroids from the progesterone family. Fibre 23 hangs freely from the lower portion of support 21.

These two types of support, 11 and 21, while being relatively flexible, have a rigid shape that holds them in the uterus and which to a certain extent opposes the movements of the uterus. For this reason, they are termed rigid supports for the purposes of the present description.

Figure 3:
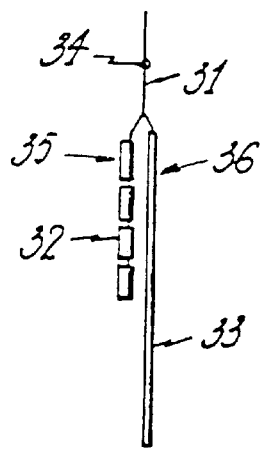
FIG. 3 shows a further embodiment of an intrauterine device of the invention, constituted by two flexible threads mounted on a filament with a means for anchoring into the tissue of the uterus.

Referring to FIG. 3, the support is constituted by a filament 31 provided with an element 34 for anchoring into the uterus tissue, suitable for insertion using a needle. Two threads 35, 36 are attached to filament 31, the threads being respectively constituted by hollow copper elements 32 for thread 35 attached one after the other to constitute a flexible thread, and for thread 36 a flexible porous polymer fibre 33 releasing steroids from the progesterone family.

Figure 4:
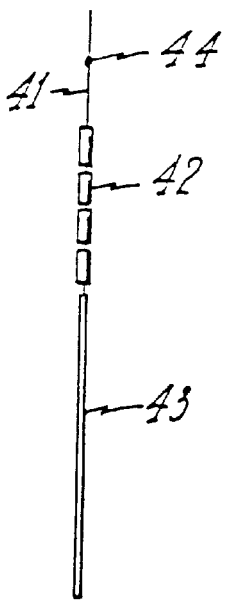
FIG. 4 shows a particularly preferred embodiment of an intrauterine device of the invention, in the form of a single flexible thread.

Finally, FIG. 4 shows a particularly preferred embodiment of the invention, in which the support is, as in FIG. 3, constituted by a filament 41 provided with an element 44 for anchoring into the uterus tissue, suitable for insertion with a needle, Fixed on this filament are, firstly, in succession, in a region close to the anchoring element 44, a succession of hollow copper elements 42, and following said hollow copper elements, and thus at a greater distance from the anchoring element 44, a porous polymer fibre 43 releasing steroids from the progesterone family, the assembly being in the form of a single thread.

These two latter embodiments, which do not retain their shape, can freely deform in the uterus, so they follow its movements without constraint. Thus, they are particularly well tolerated in the uterus.

These various embodiments of intrauterine devices allow a contraceptive treatment to be carried out that uses a combination of copper and steroids in values that are recommended by the present invention.

In accordance with the invention, the copper surface area employed is limited to a value in the range 100 to 250 $mm^2$, and the release rate of the steroid is limited to the following values, depending on the steroid used:

| | |
|---|---|
| for natural progesterone | 5 to 35 µg/day; |
| for levonorgestrel | 2 to 14 µg/day; |
| for desogestrel | 0.1 to 0.7 µg/day | i.e., in general, values in the range 10% to 70% of the minimum release rate mentioned above in current routine use for the steroid under consideration when used as an active ingredient in intrauterine contraceptive devices.

When the device is in use, the reduction in the quantity of copper present in the uterus reduces the perturbing effect that that element has on homeostasis of the endometrium. This reduction in the perturbing effect of copper is reinforced by using a steroid, while the reduced release rates used for the latter prevents or at least substantially limits the occurrence of side effects similar to those caused by release rates at the level of those employed until now. Using the device of the invention, the occurrence of side effects, both those due to the presence of copper and those due to the presence of a steroid, is avoided or at least vary substantially reduced.

In contrast, the contraceptive effectiveness of the devices of the invention is very high since the failure rate, measured over a period of use of one year, is about one per thousand.

The embodiments shown in FIGS. 2 and 4, the latter embodiment constituting a particularly preferred embodiment of the invention, have the advantage that the copper and the steroids from the progesterone family, while producing the desired synergistic effect of the present invention, each have their specific action zone.

Studies have demonstrated the significant effectiveness of copper as a contraceptive, when in the zone at the fundus of the uterus. In the embodiments shown in FIGS. 2 and 4, once the intrauterine device is placed in the uterus, the copper exerts its action on the fundus of the uterus, where it is particularly effective, while the fibre releasing the steroid can be of a length such that it exerts its action in the cervix alone. In this region, while continuing to exert its contraceptive action in the whole of the uterine cavity, and thus its contraceptive action in synergy with the copper, the steroid also exerts a protective action on the uterus against sexually transmitted ascending infections.

Because of its design in the form of a flexible thread fixed to the fundus of the uterus, the embodiment of FIG. 4 combines all the advantages cited above with the advantage that it is particularly well tolerated in the uterus, and can permanently hold the various elements constituting it in the correct position.

During tests, particularly satisfactory results were obtained using the device illustrated in FIG. 4, in which the exposed copper surface area was 200 mm², the steroid used was levonogestrel and the release rate for this steroid by the fibre was 5 to 10 μg/day.

What is claimed is:

1. An intrauterine device comprising a support and an ingredient releasing element for releasing an active ingredient, said active ingredient comprising copper and a steroid selected from the group consisting of natural progesterone, levonorgestrel and desogestrel, said copper having a surface area in the range 100 to 250 mm², and said steroid being releasable at a release rate within the following range, as a function of the steroid used:

| for natural progesterone | 5 to 35 μg/day; |
|---|---|
| for levonorgestrel | 2 to 14 μg/day; |
| for desogestrel | 0.1 to 0.7 μg/day. |

2. An intrauterine device according to claim 1, wherein said support comprises a filament having anchoring means to anchor said support into the tissue of the uterus, said ingredient releasing element comprising pierced hollow copper elements having end portions connected to form a non-rigid assembly and being arranged in an end-to-end relationship, and a flexible porous polymeric fibre, said ingredient releasing element having release means to release steroids from the progesterone group.

3. An intrauterine device according to claim 2, wherein said hollow copper elements arranged in an end-to-end relationship are secured to said filament in relative proximity to said anchoring means, and said flexible porous polymeric fibre being secured to said filament after said copper elements.

4. An intrauterine device according to claim 1, wherein said support comprises a rigid "T-shape" and wherein said ingredient releasing element releasing copper comprises a collar, and said ingredient releasing element releasing said steroid from the progesterone family and is a porous polymeric fibre positioned at a lower portion of said support.

5. An intrauterine device according to claim 4, wherein said porous polymeric fibre releasing said steroid is movably fixed to said lower portion of said support.

6. An intrauterine device according to claim 1, wherein said support comprises a rigid "V-shape" and said ingredient releasing element releasing copper comprises a copper wire wound around said lower portion of said support, and said ingredient releasing element releasing said steroid from the progesterone family comprises a porous polymeric fibre positioned at said lower portion of said support.

7. An intrauterine device according to claim 6, wherein said porous polymeric fibre releasing said steroid is movably fixed to said lower portion of said support.

8. An intrauterine device according to claim 1, wherein said ingredient releasing element for releasing copper has a release surface area of 200 mm², wherein said ingredient releasing element releases said steroid levonrgestrel at a release rate of 5 to 10 μg/day.

* * * * *